(12) United States Patent
Rodriguez et al.

(10) Patent No.: US 7,992,105 B2
(45) Date of Patent: Aug. 2, 2011

(54) SYSTEM PROCESS AND LOGIC ELEMENT FOR PROVIDING AND MANAGING RECORD KEEPING APPLICATIONS

(75) Inventors: Jose Rodriguez, Greenwood, IN (US); Katrina Rodriguez, Greenwood, IN (US)

(73) Assignee: Jose Rodriguez, Greenwood, IN (US)

( * ) Notice: Subject to any disclaimer, the term of this patent is extended or adjusted under 35 U.S.C. 154(b) by 1232 days.

(21) Appl. No.: 10/496,415

(22) PCT Filed: Nov. 21, 2001

(86) PCT No.: PCT/US01/43396
§ 371 (c)(1),
(2), (4) Date: May 21, 2004

(87) PCT Pub. No.: WO03/046800
PCT Pub. Date: Jun. 5, 2003

(65) Prior Publication Data
US 2004/0255252 A1 Dec. 16, 2004

(51) Int. Cl.
*G09G 5/00* (2006.01)
*G06F 17/00* (2006.01)
(52) U.S. Cl. .......................... 715/854; 715/968; 715/839
(58) Field of Classification Search .......... 715/762–763, 715/744–747, 705, 855, 967, 853, 854, 771–773, 715/748–749, 820–823, 826, 964, 968–970, 715/839; 709/105, 223; 345/781; 707/500, 707/740, 6, 10, 100, 101; 719/313
See application file for complete search history.

(56) References Cited

U.S. PATENT DOCUMENTS

| | | | |
|---|---|---|---|
| 5,550,971 A | 8/1996 | Brunner et al. | |
| 5,786,816 A | 7/1998 | Macrae et al. | |
| 5,966,123 A * | 10/1999 | Kaplan | 715/747 |
| 5,966,126 A | 10/1999 | Szabo | |
| 6,037,940 A | 3/2000 | Schroeder et al. | |
| 6,101,556 A * | 8/2000 | Piskiel et al. | 719/313 |
| 6,331,864 B1 | 12/2001 | Coco et al. | |
| 6,343,294 B1 * | 1/2002 | Hawley | 1/1 |
| 6,496,208 B1 * | 12/2002 | Bernhardt et al. | 715/853 |
| 6,611,846 B1 * | 8/2003 | Stoodley | 707/740 |
| 6,731,310 B2 * | 5/2004 | Craycroft et al. | 715/765 |
| 6,891,552 B1 * | 5/2005 | Bush | 715/762 |
| 7,013,298 B1 * | 3/2006 | De La Huerga | 1/1 |
| 7,039,875 B2 * | 5/2006 | Khalfay et al. | 715/762 |
| 7,337,404 B2 * | 2/2008 | Rollins | 715/747 |
| 2002/0054128 A1 * | 5/2002 | Lau et al. | 345/781 |
| 2002/0156825 A1 * | 10/2002 | Hoover et al. | 709/105 |
| 2002/0169795 A1 * | 11/2002 | Elliott et al. | 707/500 |
| 2003/0085931 A1 * | 5/2003 | Card et al. | 345/853 |
| 2006/0064415 A1 * | 3/2006 | Guyon et al. | 707/6 |
| 2007/0150562 A1 * | 6/2007 | Stull et al. | 709/223 |
| 2007/0234224 A1 * | 10/2007 | Leavitt et al. | 715/762 |

* cited by examiner

*Primary Examiner* — Steven P Sax

(57) ABSTRACT

A system, process and logic element are provided which can generate and manage an application framework by simultaneously managing the graphical user interface structures and corresponding data structures. In addition, it is possible to produce at least one list data structure which corresponds to the composite pattern data structure using an in-order sequencing procedure. At least one composite pattern data structure can be created from the corresponding list data structure based on such in-order sequencing procedure. The list data structure can be recorded in a database, a file and/or a persistence data storage arrangement. The copy of the composite pattern data structure and the corresponding instance thereof can be modified without affecting the original version of the composite pattern data structure as it existed prior to the modification.

1 Claim, 22 Drawing Sheets

FIG. 18

| Model Id | Model Type | Value Type | Value Max Size | Value Default | Value Conversion Strategy | Version |
|---|---|---|---|---|---|---|
| 10001 | C | ID | 16 | nil | nil | 0 |
| 20001 | F | ID | 16 | nil | nil | 0 |
| 30001 | S | ID | 16 | nil | nil | 0 |
| 40001 | I | String | 50 | nil | nil | 0 |
| 40002 | I | String | 50 | empty | nil | 0 |
| 40003 | I | ID | 16 | nil | nil | 0 |
| 40004 | I | Date | 20 | current | nil | 0 |

| Chart Model Id | Inorder Sequence Number | Component Model Id |
|---|---|---|
| 10001 | 1 | 10001 |
| 10001 | 2 | 20001 |
| 10001 | 3 | 30001 |
| 10001 | 4 | 40001 |
| 10001 | 5 | 40002 |
| 10001 | 6 | 40003 |
| 10001 | 7 | 40004 |
| 10001 | 8 | 30002 |
| 10001 | 9 | 40005 |
| 10001 | 10 | 40006 |

| Chart Model Id | Inorder Sequence Number | Instance Number | Value |
|---|---|---|---|
| 10001 | 1 | 10000 | General Patient |
| 10001 | 2 | 10000 | Patient Contact |
| 10001 | 3 | 10000 | Patient Identification |
| 10001 | 4 | 10000 | Doe |
| 10001 | 5 | 10000 | John |
| 10001 | 6 | 10000 | 11112222 |
| 10001 | 7 | 10000 | 2001-08-16 |
| 10001 | 8 | 10000 | Patient Address |
| 10001 | 9 | 10000 | 111 America Drive |
| 10001 | 10 | 10000 | New York, NY 10001 |

1400

SYSTEM PROCESS AND LOGIC ELEMENT FOR PROVIDING AND MANAGING RECORD KEEPING APPLICATIONS

CROSS-REFERENCE TO RELATED APPLICATION(S)

This application is a national stage application of PCT Application No. PCT/US01/43396 which was filed on Nov. 21, 2001 and published on Jun. 5, 2005 as International Publication No. WO 03/046800 A1 (the "International Application"), the disclosure of which is incorporated herein by reference in its entirety.

FIELD OF THE INVENTION

The present invention relates to a computer-based system, process, and logic element for organizing, recording, and displaying medical patient care information. In particular, the system, process and logic element are implemented via an application framework that may create and update visual graphical user interface structures for e.g., a notebook widget, while simultaneously possibly managing a composite pattern data structure (or tree data structure).

BACKGROUND OF THE INVENTION

The provision of health care services to patients depends on the maintenance of a substantial amount of patient information, including both medical information relating to patient treatment(s) and non-medical information utilized for administrative purposes.

In the past, certain health care providers maintained patient information manually on multitudes of physical paper forms that correspond to segments of medical and non-medical patient information. The total set of collected medical and non-medical information forms for a patient constitutes a patient chart. Health care providers generally create these forms to define and record one or more segments of the patient information for a particular medical need (e.g. an assessment tool, a medical history, a physician order, etc.) or non-medical need (e.g. contact information, insurance information, referral, billing, etc.). The data items on the forms can be referred to as "Charting Items". Some examples of medical Charting Items for an assessment tools form are heart rate, temperature, blood pressure and weight. Some examples of non-medical Charting Items for contact information form are name, address, phone and insurance number. The maintenance of the patient includes the maintenance of these individual Charting Items.

The maintenance of the patient information in physical charts has several disadvantages. In particular, the physical charts can be lost or damaged. Also, the data integrity can often be compromised on the physical charts due to illegible handwriting, or careless annotation and marks. The forms and Charting Items can also be created ad hoc, and may change without a consensus from other medical practitioners. In addition, the medical terminology and practices constantly change, and/or become obsolete. Furthermore, the duplication of the information can also present a problem because many forms may require basic information, such as vitals, contact or insurance information as part of the treatment or identification, and this information is often duplicated from one form to another.

The conventional electronic patient charting information systems and methods also have certain disadvantages. In particular, prior art patient charting applications are designed similarly to the traditional computer software systems, often ignoring the dynamic nature of the problems associated with the physical patient charts. Also, technologies such as relational databases and procedural (or structured) programming languages are not intended to be used in a dynamic manner, which is the nature of the current patient charts. Indeed, the traditional methods for automating the maintenance of the patient information, which utilize relational databases, do not meet the demands of the ever-changing patient charting environment. The relational databases have shortcomings when the Charting Items are added to the database structure that require a re-generation of the database and re-copying of the data.

The prior art methods and systems for entering and viewing information also do not emulate the physical forms that are used for the patient information. In particular, the graphic screens are traditionally designed for one-time data capture of information, and the entry of the data on a screen-by-screen basis, in a sequence, is often confusing to the user. The navigation through a succession of the screens is a cumbersome and costly operation if only a single change is required. The screens also have a similar drawback as that of the databases, e.g., when adding the Charting Item. For example, when another Charting Item is added, the screen must be regenerated from the development level by the conventional systems and methods. The health care providers often have to adapt new practices in order to utilize the current charting systems. These changes have to be implemented by the software engineers who are not familiar with the medical field. Thus, the necessary changes may not necessarily be implemented in a proper or accurate manner.

The problems inherent in the general-purpose databases and the conventional patient information databases illustrate a need for a system, process and logic element that are flexible for organizing, recording and displaying medical patient care information. Additionally, there exists a need for a system, process and logic element which are easy to use, and can be learned by the medical personnel who have limited experience with computers or software systems.

SUMMARY OF THE INVENTION

It is therefore the object of the present invention to overcome the deficiencies associated with the prior art.

Accordingly, an exemplary embodiment of a system, process and logic element are provided for creating an application framework according to the present invention. In particular, at least one graphical user interface ("GUI") structure can be generated. Simultaneously with the generation of the GUI structure, at least one corresponding composite pattern data structure can be generated. In addition, it is possible to produce at least one list data structure which corresponds to the composite pattern data structure using an inorder sequencing procedure. Also, at least one composite pattern data structure can be created from the corresponding list data structure based on this inorder sequencing procedure. The list data structure may be recorded in a database, a file and/or a persistence data storage arrangement.

In another embodiment of the present invention, the GUI structure can be associated with at least one node of the corresponding composite pattern data structure, and such association being based on a type of data contained within the node. Also, the GUI structure may includes a notebook-type GUI structure, which emulates a physical folder for maintaining electronic forms. The composite pattern data structure and/or the GUI structure can be modified.

In yet another embodiment of the present invention, the GUI structure and the corresponding composite pattern data structure can be obtained. Then, it is possible to allow for the modification of the GUI structure, while simultaneously modifying the composite pattern data structure.

In still another embodiment of the present invention, at least one copy of the composite pattern data structure can be created. Then, at least one instance of this copy may be produced. The copy of the composite pattern data structure and the corresponding instance thereof are capable of being modified without affecting the original version of the composite pattern data structure as it existed prior to the modification.

According to another embodiment of the present invention, the composite pattern data structure is capable of being modified without affecting the copy of the composite pattern data structure and the corresponding instance thereof. Also, at least one node of the composite pattern data structure can be associated with an element of the GUI structure based on the data contained in the node. Also, the notebook-type interface can emulate a physical folder for maintaining electronic forms.

The system, process and logic element can provide data independence, e.g., by creating clones or copies of the one or more data structures, such that modification of one instance of a data structure will not impact the other data structures. Additionally, the system, process and logic element of the present invention is preferably independent of method of the data storage. This can be accomplished, e.g., by using a traversal procedure for converting the composite data structure into a simple list format that can be stored in any manner that the user selects (e.g., in a file, a database, etc.).

BRIEF DESCRIPTION OF THE DRAWINGS

For a more complete understanding of the present invention and its advantages, reference is now made to the following description, taken in conjunction with the accompanying drawings, in which:

FIG. 18 shows an exemplary Model Attribute Table and its sample entries according to one embodiment of the present invention.

FIG. 20 shows an exemplary Chart Structure Organization List for the exemplary chart prototype data structure of FIG. 19.

FIG. 22 shows an exemplary instance list for the patient chart of FIG. 21.

DETAILED DESCRIPTION OF THE INVENTION

An exemplary embodiment of a system, process and software arrangement for structuring a computer software application according to the present invention are provided. In particular, this exemplary embodiment provides an application framework which defines various data structures, interrelationships between entities in those data structures and their functions, and methods for their use in certain record keeping applications.

The exemplary embodiment of a system, process and logic element according to the present invention can be used within the context of the medical field, e.g., in the patient charting practice of a medical office clinic, and hereinafter will be referred to as a "chart organizer" for the sake of simplicity. However, it should be understood that various embodiments of the present invention can also be used to implement flexible computer-based record keeping systems and processes for a number of different uses in various fields, including applications in financial organizations, banking, retail inventory control, human resources, etc.

Figure 1:
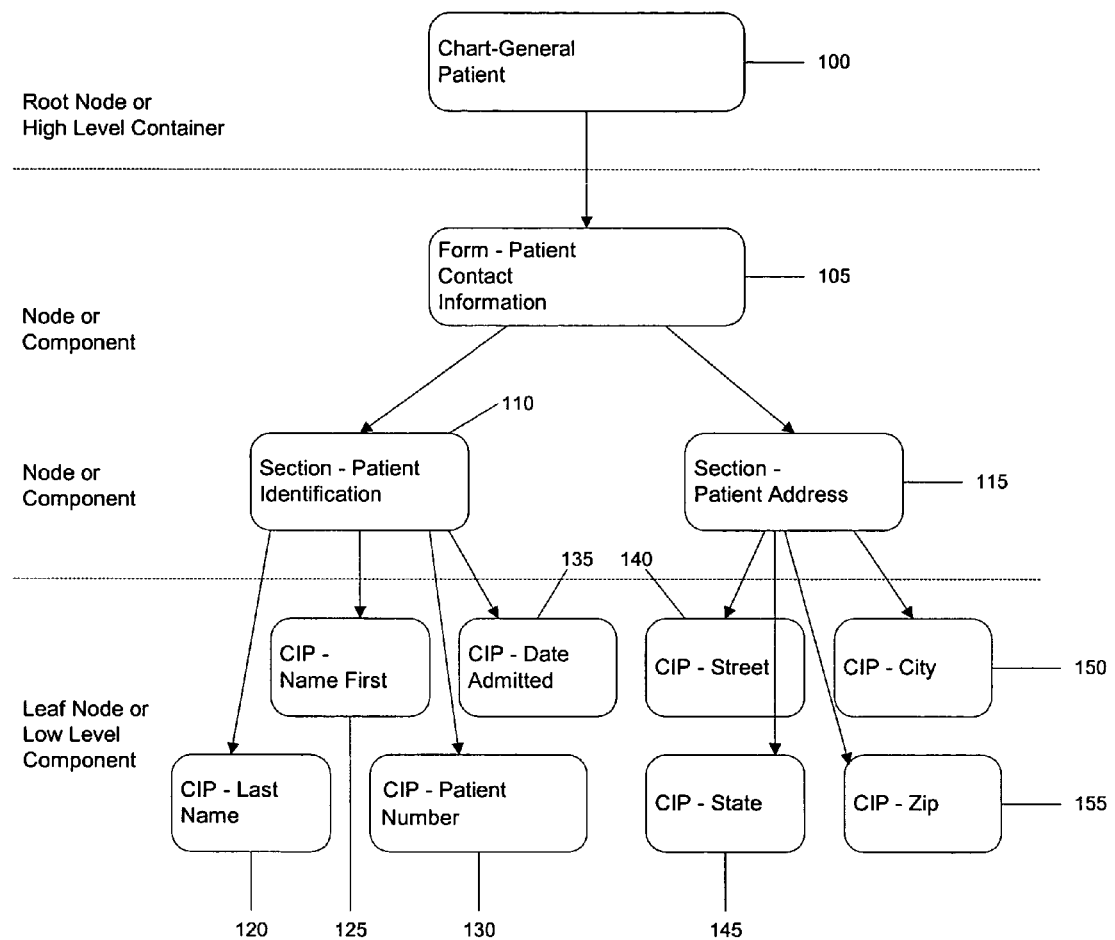
FIG. 1 shows an exemplary chart prototype data structure used in an exemplary embodiment of a system according to the present invention which can be utilized in the medical field.

According to an exemplary embodiment of the present invention, the chart organizer comprises a tree-type or composite data structure, as illustrated in FIG. 1, which is composed of the following simple entities: "Chart Prototype 100", "Form 105", "Section 110, 115" and "Charting Item Prototype 120-135". The Chart Prototype 100 is a data entity which can act as a model or template for a patient chart, and may define medical and non-medical information that is to be recorded for a patient. It can further define a type of patient classification and the required information for such patient. A Chart Prototype comprises a collection of Forms. Each Form can be used to represent a segment of information that the health care organization prefers to maintain. A set of Forms is determined by the patient type within the practice, particular health care a patient is scheduled to receive (e.g., medical information), and the administrative information needed by the health care organization to process the information for the patient.

The Forms can be used in various ways. For example, a Chart Prototype—"General Patient"—may consist of a set of Forms (e.g., Forms A, B, and C), and a Chart Prototype—"Orthopedic Patient"—may consist of another set of Forms (e.g., Forms A, B, and D). Note that there may be common Forms there between, and other non-common Forms which are particular to the specific classification of the patient. Additional charts can be created as hybrids of these Forms, such as a Chart Prototype—"Orthopedic Surgery Patient"—which consists of yet another set of Forms (e.g., Forms A, B, D, G). The number of different types of charts and combinations that may be created is unlimited.

Referring again to FIG. 1, the Form 105 is shown to be a collection of the Sections 110, 115, each representing a segment of the patient information. The Section 110 is a collection of the Charting Item Prototypes 120-135, and represents a sub-segment of the Form 105. The Sections 110, 115 are the electronic equivalents of pages within a physical paper form. In this exemplary embodiment of the present invention, the Form "Patient Contact Information" 105 has the Section 110 referred to as "Patient Identification Section," which contains e.g., Charting Item Prototypes "Name First" 125, "Name Last" 120, "Date Admitted" 135, and "Patient Number" 130. The Form 105 also contains other another Section 115—"Patient Address"—which contains certain charting items, e.g., "Street" 140, "City" 150, "State" 145, and "Zip" 155.

The Charting Item Prototype is an entity used to define the data for charting the patient information. This Charting Item Prototype has properties which serve as the specification (or metadata) for the data. It defines the properties of the type of data which can be stored, the corresponding graphical user interface (hereinafter "GUI") entities, and storage and usage attributes for the data. The Charting Item Prototype can be re-used on any Section. Provided below is an example of the Charting Item Prototype's properties in one exemplary embodiment of the present invention:

| Property | Property Description | Property type |
|---|---|---|
| Name | Identify Charting Item | 32 Characters text |
| Description | Text description | 1000 Character text |
| Data type | Type of data represented (i.e. String, Integer, Date etc.) | List of choices |
| Valid Values | Values used for data validation | List of choices |
| Length | Length of largest data representation | Integer |
| Category | Category if data can be classified | 32 Characters text |
| ID | Unique numerical identification | 32 Character text |
| Date Created | Version of property | Date |

Chart Prototype Data Structure

FIG. 1 also illustrates the interrelationship of the various entities within the chart prototype data structure, which can be implemented as a tree-type data structure in the structured programming terms, and as a composite pattern in the object oriented programming terms. Preferably, each of the different entities within the chart prototype data structure has a predefined role.

As shown in FIG. 1, the Chart Prototype 100 relates to a root node in the tree-type data structure and the top-level container in the composite pattern. This means that this data entity can only be used to point to other data entities. The Chart prototype 100 may contain Forms, and would not preferably be a part of another data entity. The Form 105 relates to a node in the tree-type data structure, and a component in the composite pattern. This data entity can be contained by another data entity, and may be used to point to other data entities. In this exemplary embodiment, the Form 105 contains (or points to) the Sections 110, and is contained (or pointed to) in the Chart Prototype 100. These Sections 110, 115 also relate to a node in the tree-type data structure and a component in the composite pattern. This data entity can be contained in (or pointed to by) another data entity, and may be used to hold (or point to) other data entities. The Section 110 contains the Charting Items 120-135, and is contained in (or pointed to by) the Form 105.

The Charting Item Prototype described above relates to a leaf node in the tree-type data structure, being the lowest level component in the composite pattern. This data entity is contained in (or pointed to by) another data entity, and cannot be used to hold (or point to) other data entities. The Charting Item Prototype of the exemplary embodiment of the present invention can be used to represent a data item which is adapted to be used for patient charting.

Notebook GUI Widget

Figure 2:
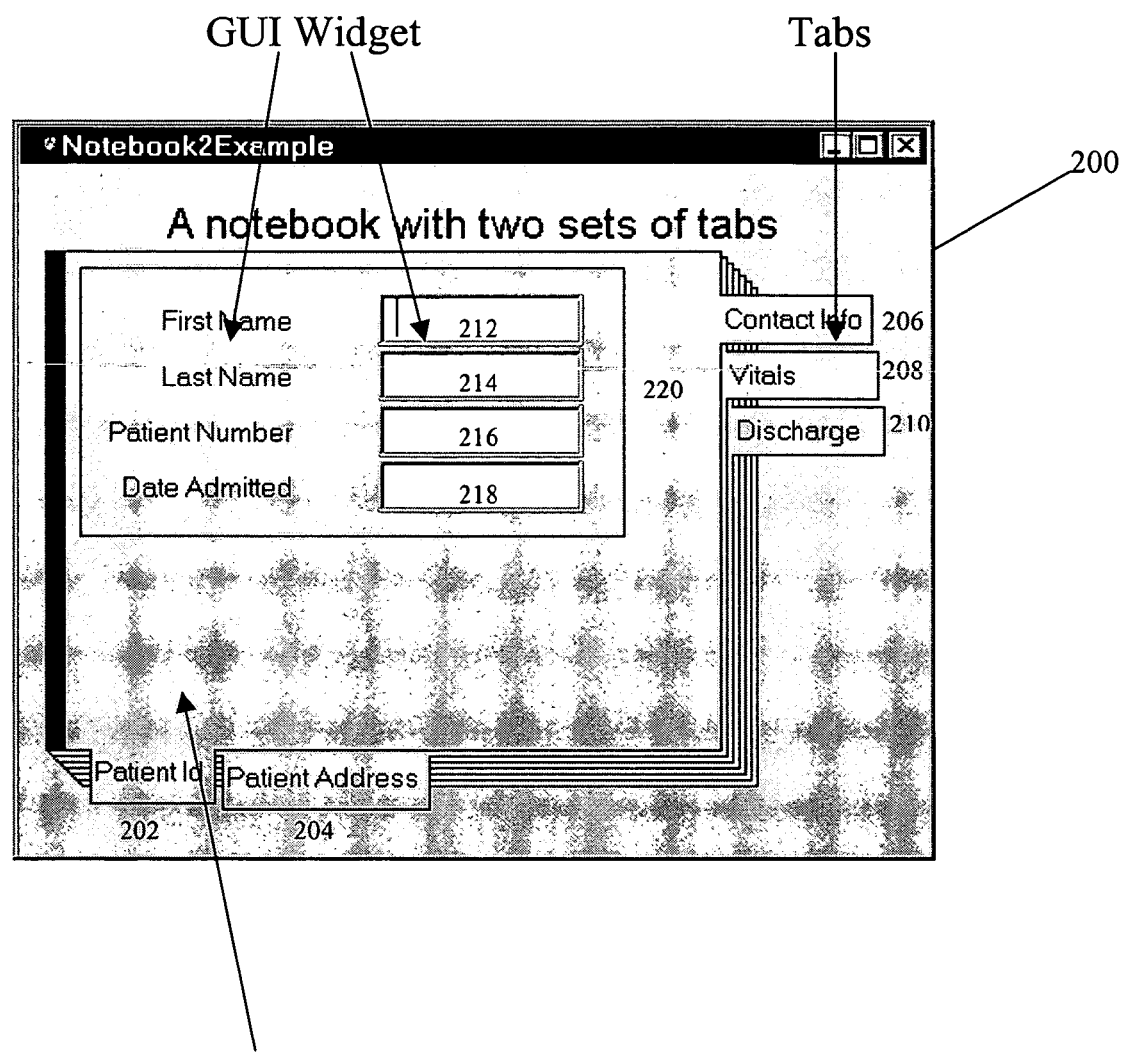
FIG. 2 shows an exemplary illustration of a graphical user interface notebook widget used in an exemplary embodiment of the system according to the present invention.
Figure 3:
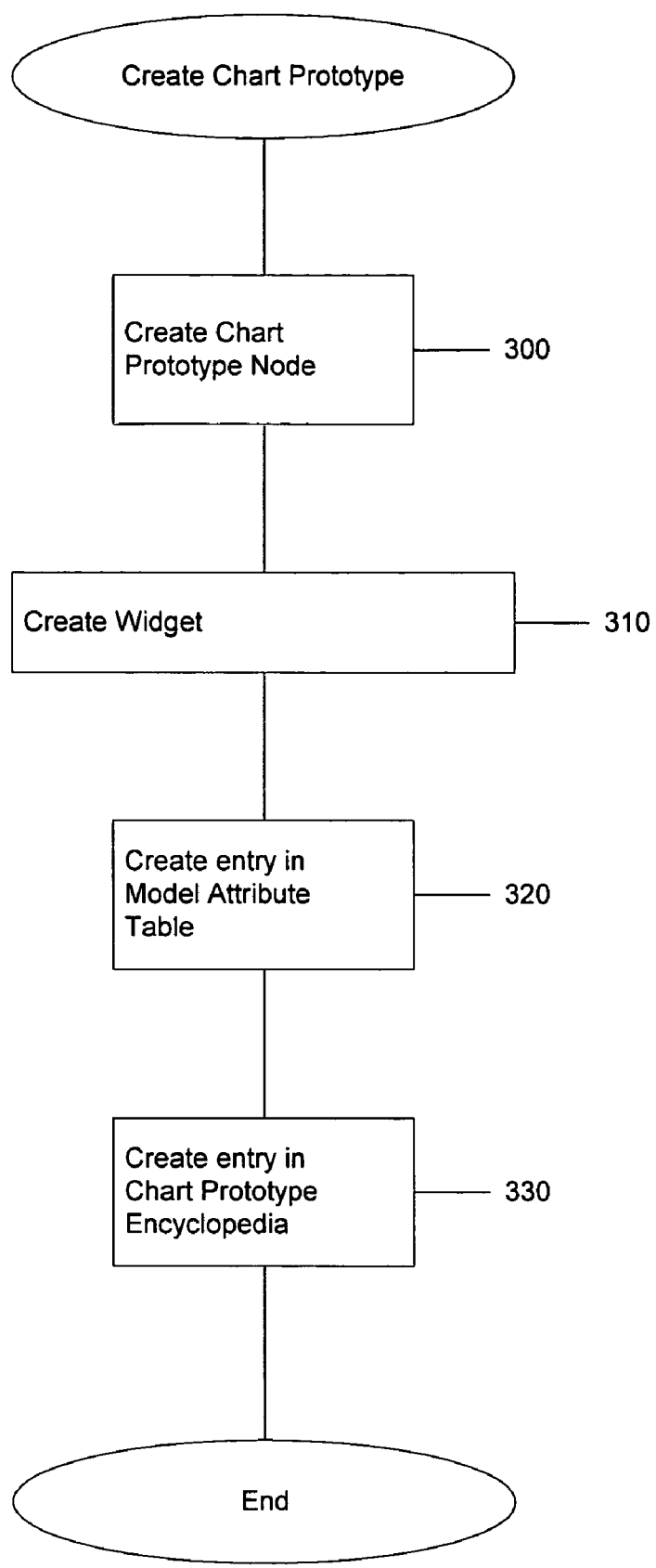
FIG. 3 shows an exemplary flow diagram of an exemplary embodiment of a process according to the present invention for generating a patient chart.
Figure 4:
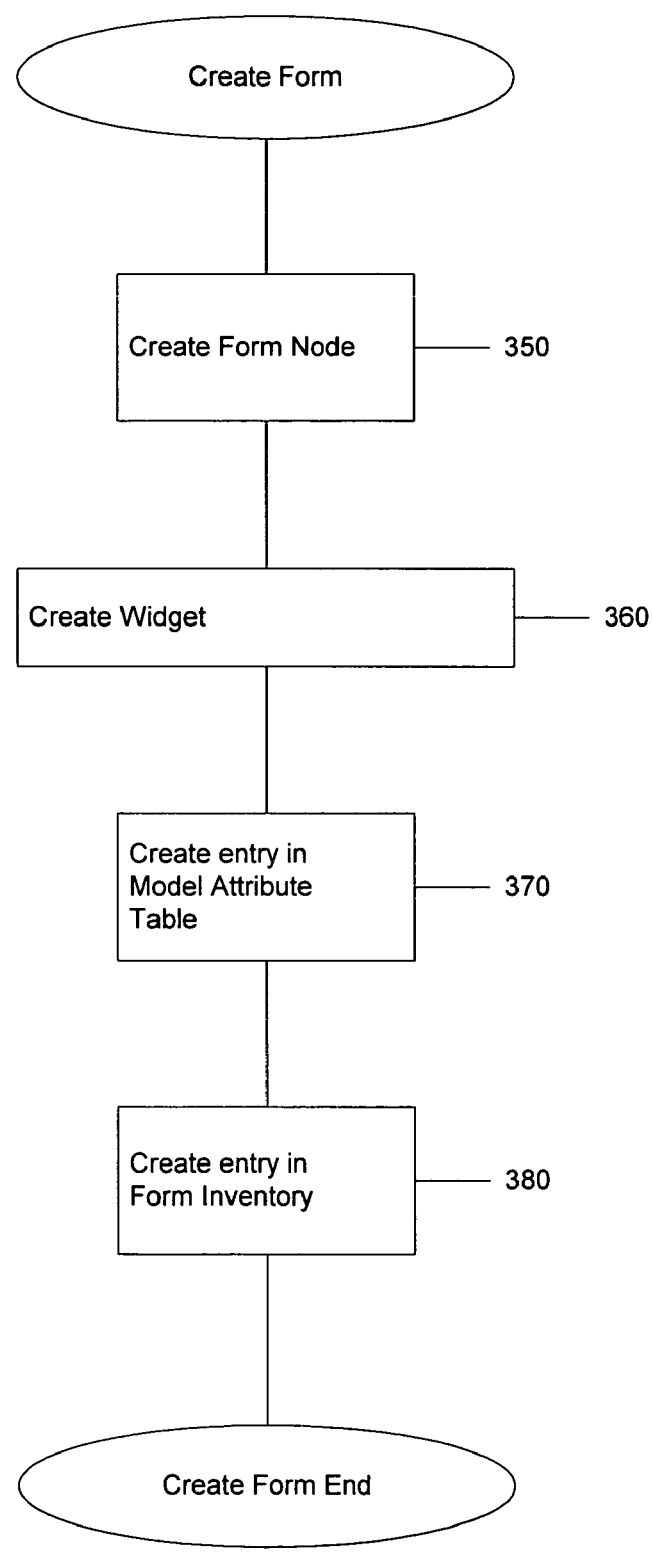
FIG. 4 shows an exemplary flow diagram of another exemplary embodiment of the present invention for generating a Form.
Figure 5:
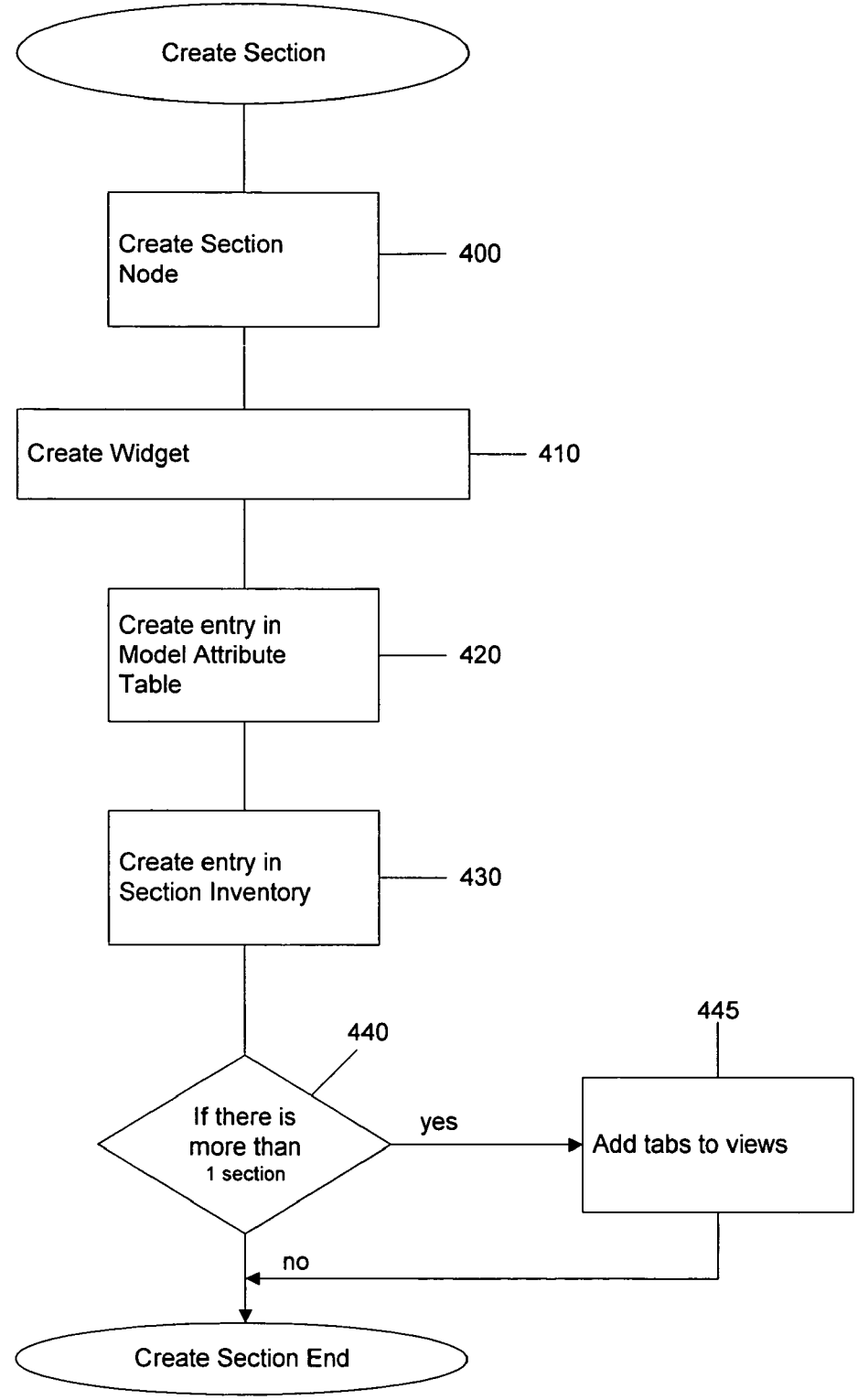
FIG. 5 shows an exemplary flow diagram of an exemplary embodiment of the present invention for generating a Section.
Figure 6:
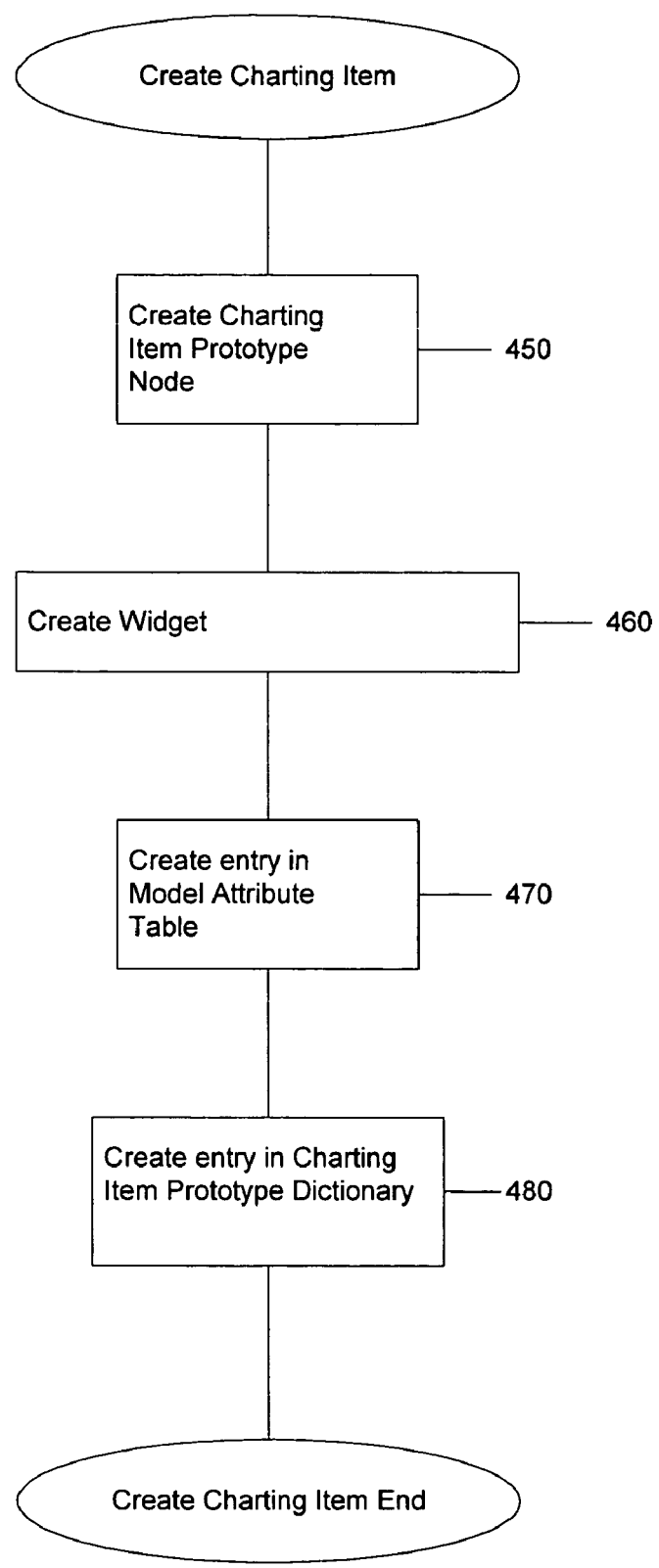
FIG. 6 shows an exemplary flow diagram of an exemplary embodiment of the present invention for generating a Charting Item.
Figure 7:
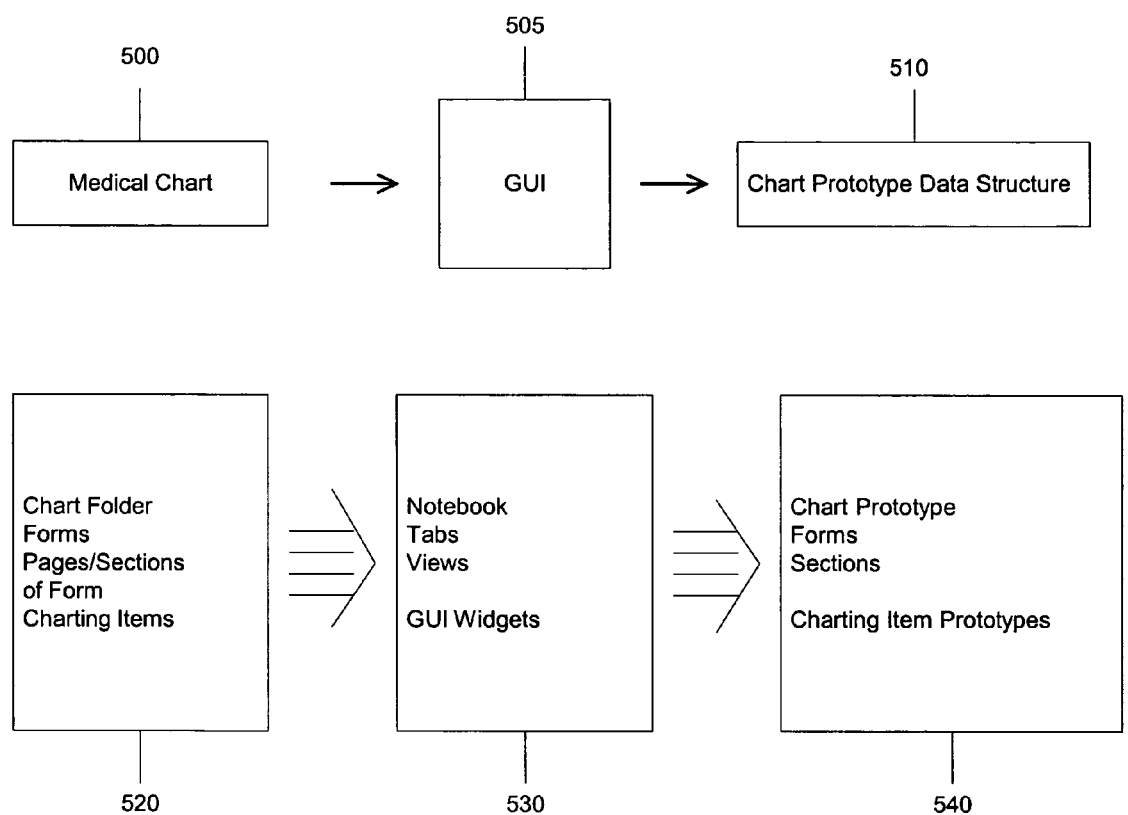
FIG. 7 shows exemplary interrelationships between a physical patient chart, a data structure of a medical chart, and corresponding graphical user interface entities according to another embodiment of the present invention.

FIG. 2 shows an exemplary notebook Graphical User Interface ("GUI") widget 200 that can be utilized in conjunction with the chart prototype data structure of FIG. 1. For example, this widget 200 can be useful as an interface for the users because it is based on a concept that is familiar to most people, and requires little training for the users. The GUI widgets are generally used to represent data within a view. Various different types of the GUI widgets (such as buttons, text, input fields, and lists) can be used to display data and receive user input data. As illustrated in FIG. 2, the notebook GUI widget 200 may include tabs which are displayed to provide access to each Form and each Section within the respective Form. Each Section defines a view, which is what can be seen in the respective Section, and may contain and display any combination of the GUI widgets for various purposes. As illustrated in FIG. 2, tabs 206-210 represent the Forms, each of which may contain one or more Sections. The Form tab 206—"Contact Info"—is selected in this example, and has particular Sections 202, 204. The Section tab 202 is also shown to be selected, thus "Patient ID" is displayed in the current view 220. This current view 220 provides access to the Charting Items such as "First Name" 212, "Last Name" 214, "Patient Number" 216 and "Date Admitted" 218. The Section tab 204 may alternatively be selected, and is capable of displaying the view for the "Patient Address" information section.

Notebook Composite Organizer Controller

In an exemplary embodiment of the present invention, a "Notebook Composite Organizer Controller" can be used to interact with the med-chart organizer for creating and modifying the patient charts. Most conventional physical patient charting systems and processes are organized in folders that consist of a collection of forms. The above-described notebook GUI widget 200 preferably emulates a physical folder of forms, and may use a chart prototype data structure which is a data structure that also emulates a physical folder of forms. In the exemplary embodiment of the present invention, the Notebook Composite Organizer Controller can associate the notebook GUI widget 200 within the chart prototype data structure to form a software framework which can be used to create and update the charts, as well as process the patient chart information.

According to this exemplary embodiment of the present invention, the Notebook Composite Organizer Controller can generate the charts during a chart maintenance process, which can simultaneously manage both the notebook GUI widget 200 and the chart prototype data structure, create a persistence specification for the chart prototype data structure, add entries into a "Model Attribute Table" (as shall be discussed in further detail below), and update inventories for the charting entities. The Notebook Composite Organizer Controller can also process the patient chart information during the patient charting process. For example, this patient charting process can translate the data between the data storage arrangement and the display of the notebook GUI widget 200, allow the patient chart to dynamically change its structure, and manage the persistence specification for the patient chart.

Exemplary Details of the Chart Maintenance Process

The Notebook Composite Organizer Controller can be used to interact with the chart organizer for creating charts, and incorporates the chart maintenance process as the process for creating and updating medical charts. The chart maintenance process is preferably the chart organizer's implementation of a chart maintenance model, which can be a model of a process used to create and update the medical charts. Any medical professional or other user can use this model to define the patient chart, either with or without the software used for such definitions.

FIGS. 3-6 show exemplary embodiments of the chart maintenance process implementations of a create a Chart Prototype, a Section and a Charting Item, respectively. These processes are substantially similar to one another. For example, during the chart maintenance process, the following general tasks can be performed for any of the different charting entities (see FIGS. 3-6):

a) Create a node for the chart prototype data structure (steps 300, 350, 400, 450);
  b) Create a corresponding widget (steps 310, 360, 410, 460).
  c) Create an entry in a Model Attribute Table (steps 320, 370, 420, 470)
  d) Create an entry of the node in the list of the charting entity (steps 330, 380, 430, 480).
  e) For creating the Sections, determine whether there are multiple sections 440, and if so, add tabs to the views 445.

When the chart maintenance process is completed for a particular chart, the chart prototype data structure and the notebook GUI widget 200 that the process previously created are recorded, and a chart structure organization list which defines the persistence specification for the instances of the charting prototype data structure is generated (See FIG. 14), as shall be described in further in detail below. The following is a detailed description of the various steps in the exemplary embodiment of the chart maintenance process according to the present invention.

Figure 8:
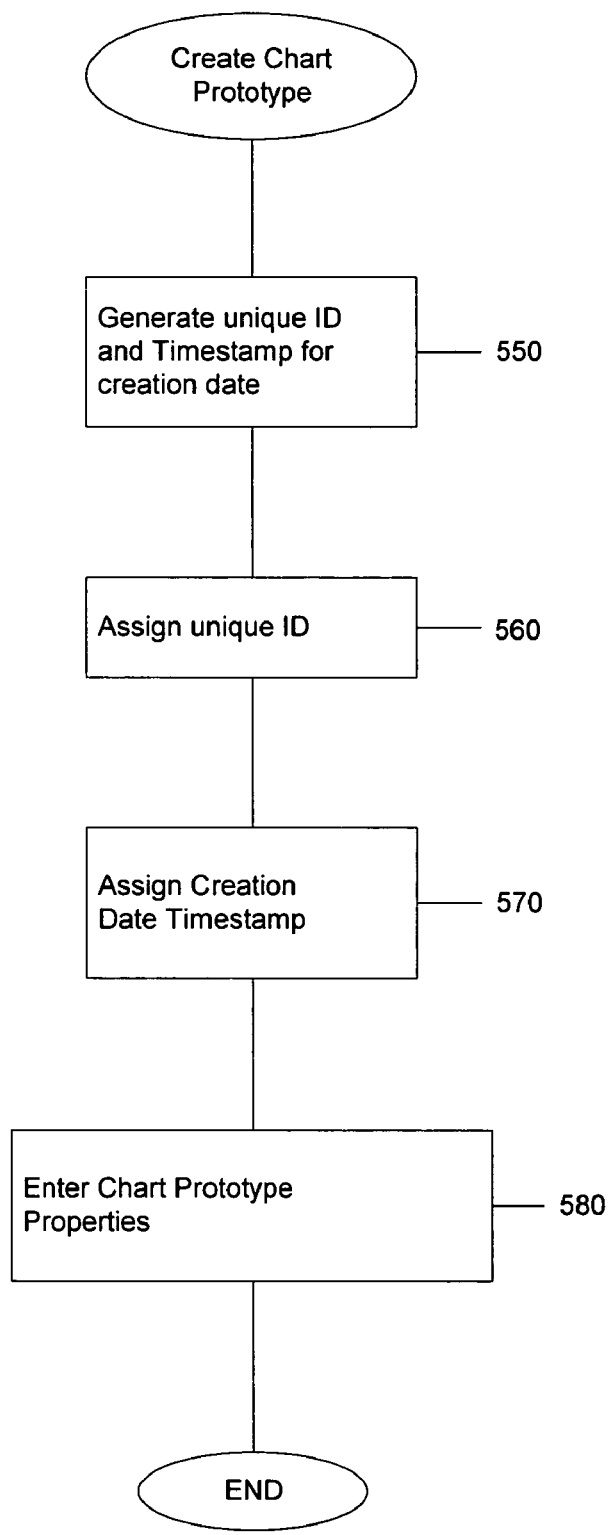
FIG. 8 shows an exemplary flow diagram for creating a Chart Prototype Node in a Chart Maintenance Process according to the exemplary embodiment of the present invention.

In particular, the first procedure preferably creates a node for the chart prototype data structure (e.g., see steps 300, 350, 400, 450). Referring to FIG. 8, the following substeps are performed to create the various nodes in the data structure:

a) Generate unique identification and timestamp (step 550);
  b) Assign node identification ("ID") and timestamp (steps 560, 570);
  c) Enter properties for node (step 580); and
  d) Add node to target.

Substeps (a) and (b) may be identical for every node. Substep (c), where certain properties for the node are entered, can differ from one node to another, e.g., due to the type of information being entered for each node. In substep (d), the node can be added to a target data structure, where the node is actually added within the chart prototype data structure.

Provided below is an exemplary embodiment for creating each node in the chart prototype data structure according to the present invention. As shown in FIG. 8, the user creates a chart prototype node in step 550, and a unique numerical identification ("ID"), and a timestamp for the creation date is preferably generated. Then, in step 560, this unique numerical ID is assigned to the chart prototype. In step 570, a timestamp for the creation date is assigned to the chart prototype, and in step 580, certain properties (e.g., metadata information) are entered for the chart prototype.

Figure 9:
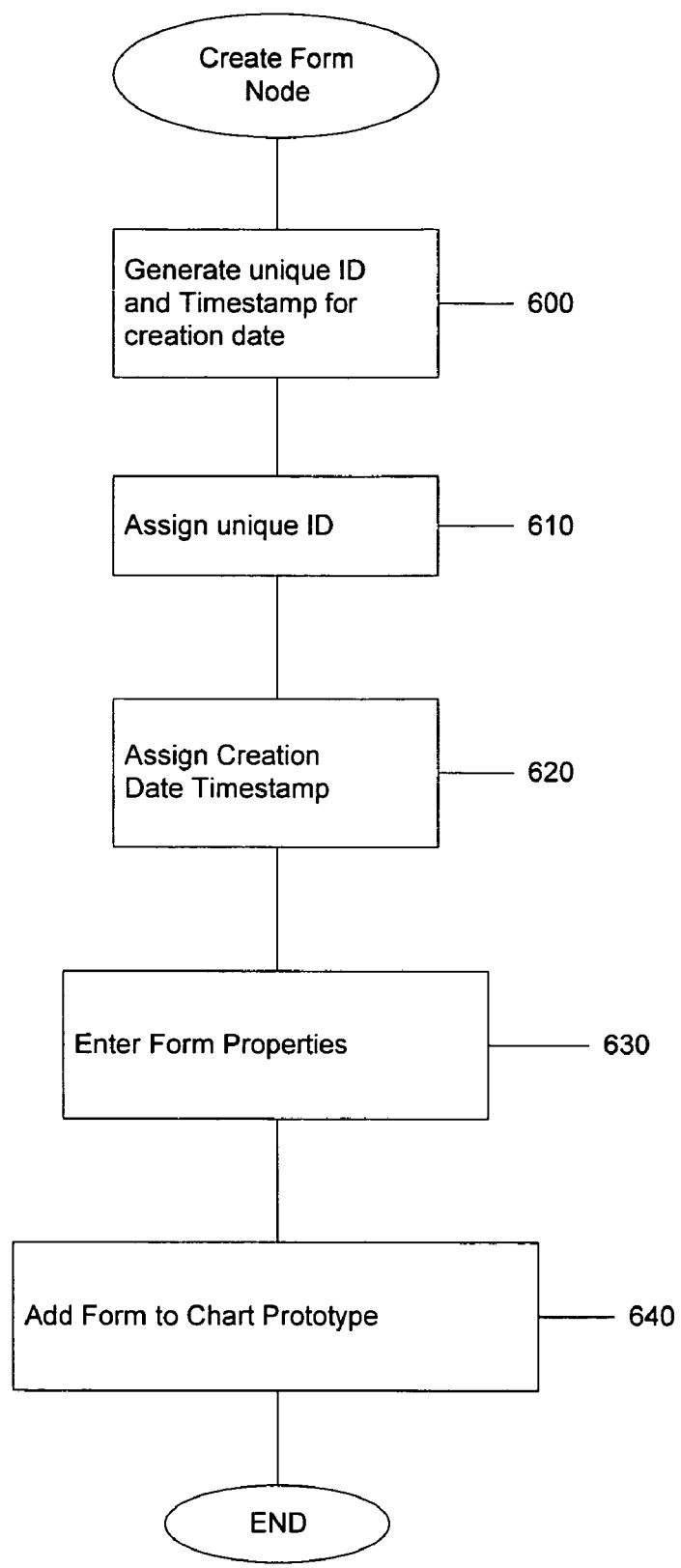
FIG. 9 shows an exemplary flow diagram for creating a Form Node in the Chart Maintenance Process according to the exemplary embodiment of the present invention.

FIG. 9 shows the exemplary creation of the Form nodes. In particular, a unique numerical ID and a timestamp for the creation date of a particular Form node are generated in step 600. Then, in step 610, a unique numerical ID is assigned to the respective Form, and the timestamp is generated in step 620. Certain properties (e.g., metadata information) can be set for the respective Form in step 630. Thereafter, this Form may be added to the chart prototype in step 640.

Figure 10:
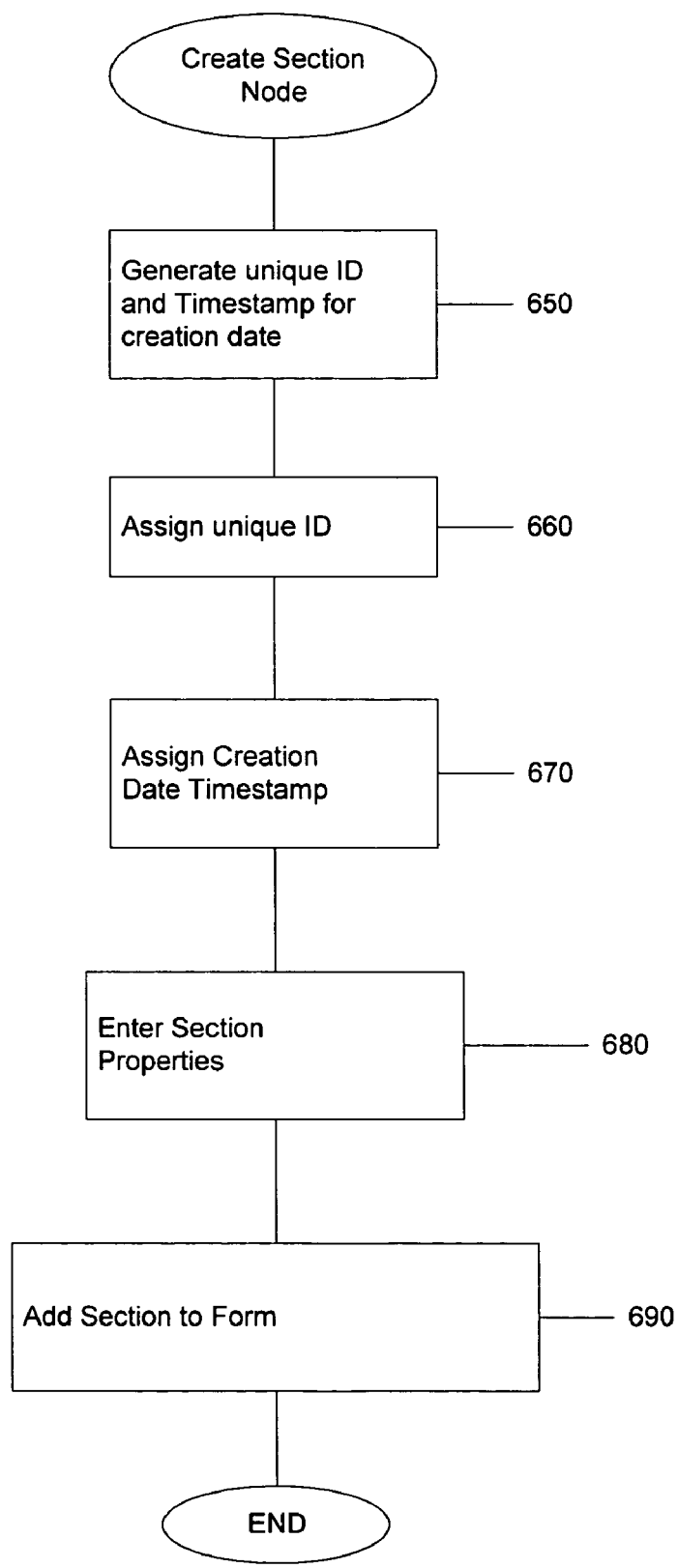
FIG. 10 shows an exemplary flow diagram for creating a Section node in the Chart Maintenance Process according to the exemplary embodiment of the present invention.
Figure 11:
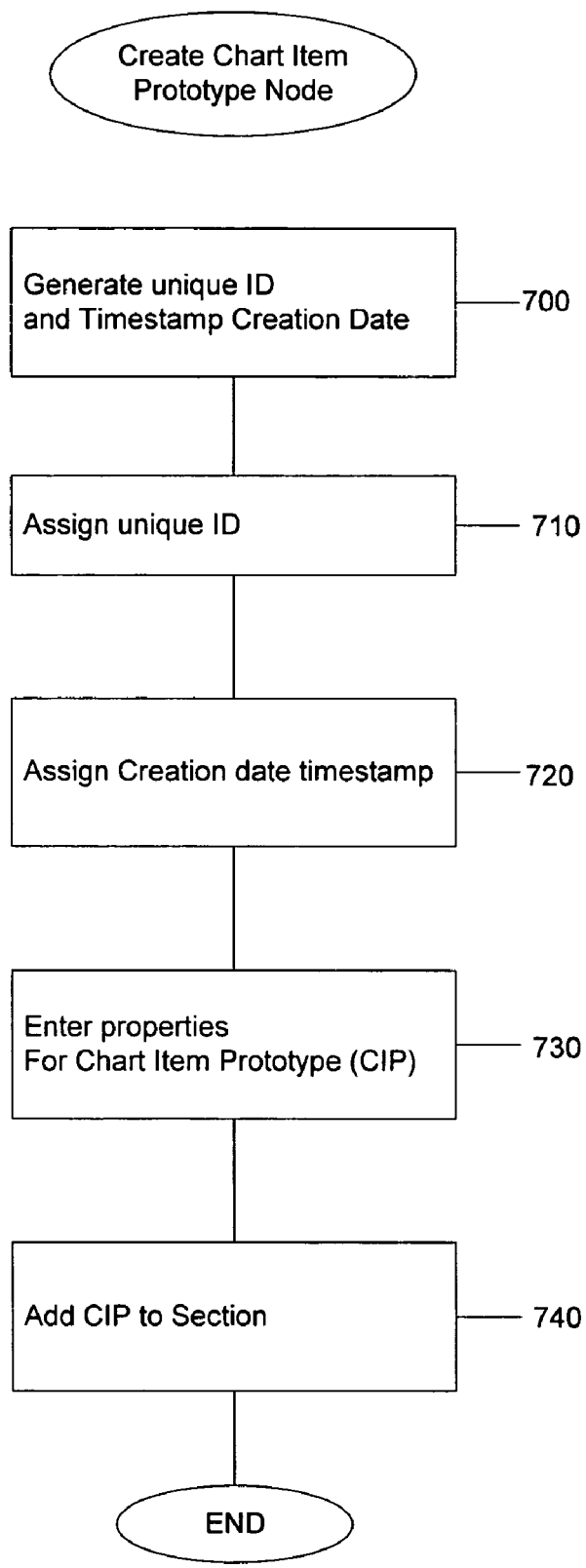
FIG. 11 shows an exemplary flow diagram for creating a Charting Item Prototype node according to the Chart Maintenance Process in the exemplary embodiment of the present invention.

As shown in FIG. 10, the Section nodes are created in a similar manner. In particular, a unique numerical ID and a timestamp for the creation date of a particular Section node are generated in step 650. Then, in step 660, the unique numerical ID is assigned to the respective Section, and a timestamp is generated in step 670. Again, particular properties (e.g., metadata information) can be set for the Section in step 680. Thereafter, this Section may be added to the Form in step 690.

FIG. 10 shows that the Chart Item Prototype ("CIP") nodes are created in a similar manner. In particular, a unique numerical ID and a timestamp for the creation date of the Chart Item Prototype node are generated in step 700. Then, in step 710, the unique numerical ID is assigned the CIP node, and the timestamp is generated in step 720. Further, certain properties (e.g., metadata information) can be set for the Chart Item Prototype in step 730. Thereafter, the Chart Item Prototype may be added to the Section in step 740.

Figure 12:
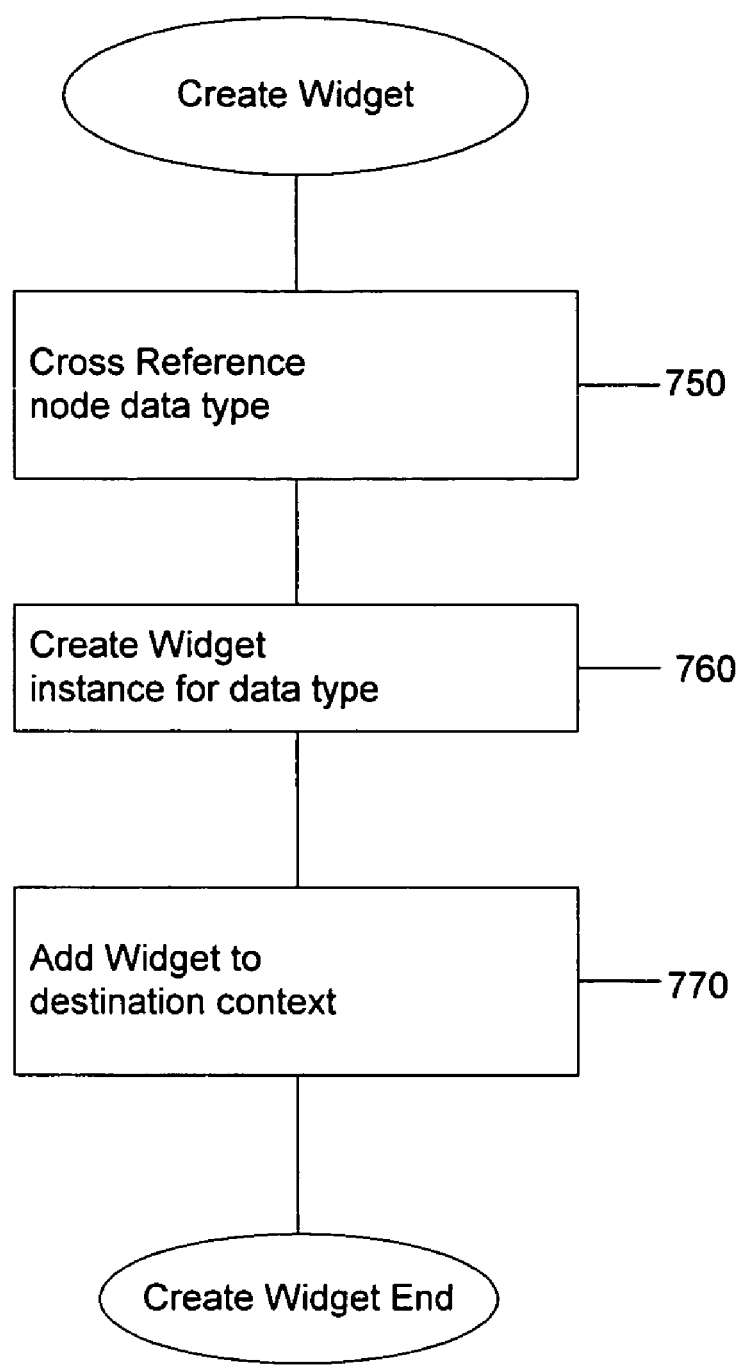
FIG. 12 shows an exemplary flow diagram for creating a Graphical User Interface widget in the Chart Maintenance Process according to the embodiment of the present invention.

When the chart prototype data structure node is defined, as described above, a widget can be created using the exemplary procedure which is shown in FIG. 12. In particular, the system and process of the present invention can implement the exemplary procedure of FIG. 12 to create the widget for the notebook GUI structure with relation to a node in the data structure. In particular, in step 750, the node and the data type can be cross-referenced to locate the widget. In step 760, an instance of the widget is created for the data type. Thereafter, the widget is added to the destination context in step 770.

Steps 750 and 760 can generally be used for every node. Also, step 770 determines the context in which the widget should be added. The following chart illustrates the associations for adding the widgets according to an exemplary embodiment of the present invention.

| Node | GUI Widget | Context |
| --- | --- | --- |
| Chart Prototype | Notebook Widget | none (root) |
| Form | Tab | Notebook Widget |
| Section | View | Tab |
| Charting Item Prototype | Item Widget | Widget |

Figure 13:
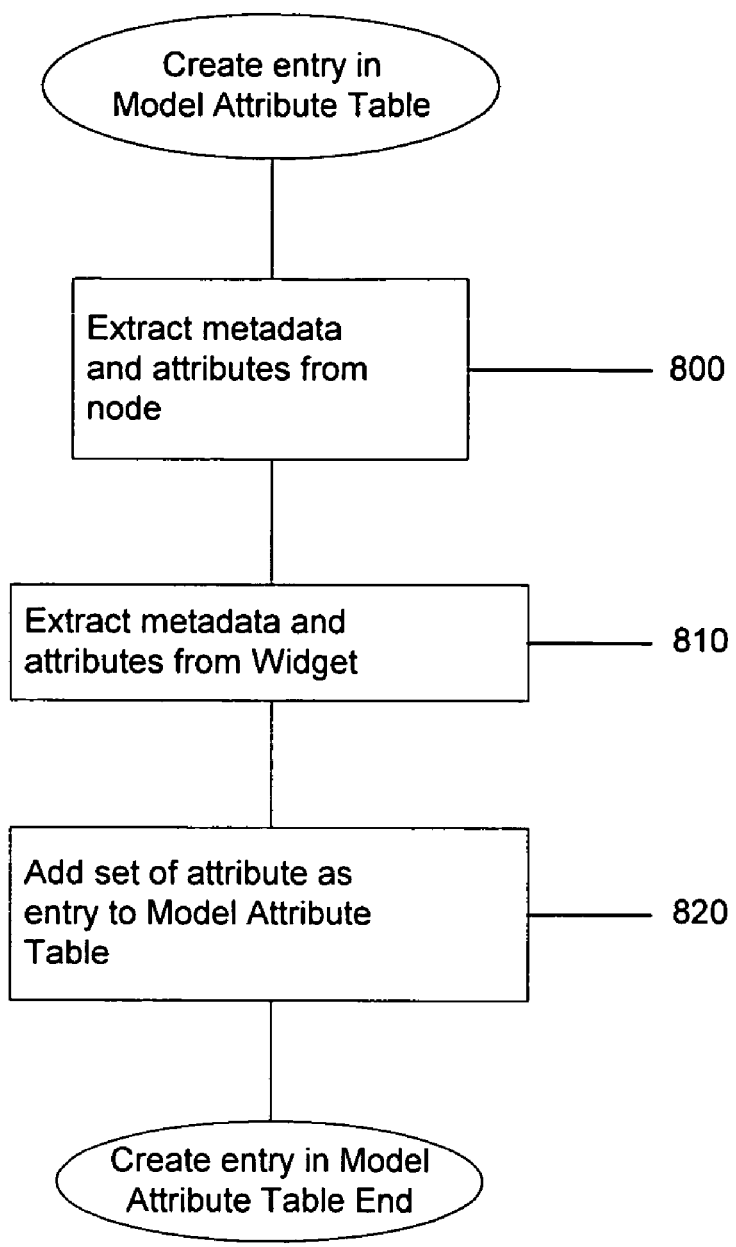
FIG. 13 shows an exemplary flow diagram for creating an entry Model Attribute table in the Chart Maintenance Process according to the embodiment of the present invention.

After the widget is created using the procedure shown in FIG. 12 and described above, an entry in the Model Attribute Table can be generated using another procedure, the details of which are shown as a flow diagram in FIG. 13. In particular, metadata and certain attributes can be extracted from the node in step 800. Other metadata and attributes are then extracted from the widget (step 810). Thereafter, the set of extracted attributes are added to the Model Attribute Table in step 820.

Figure 14:
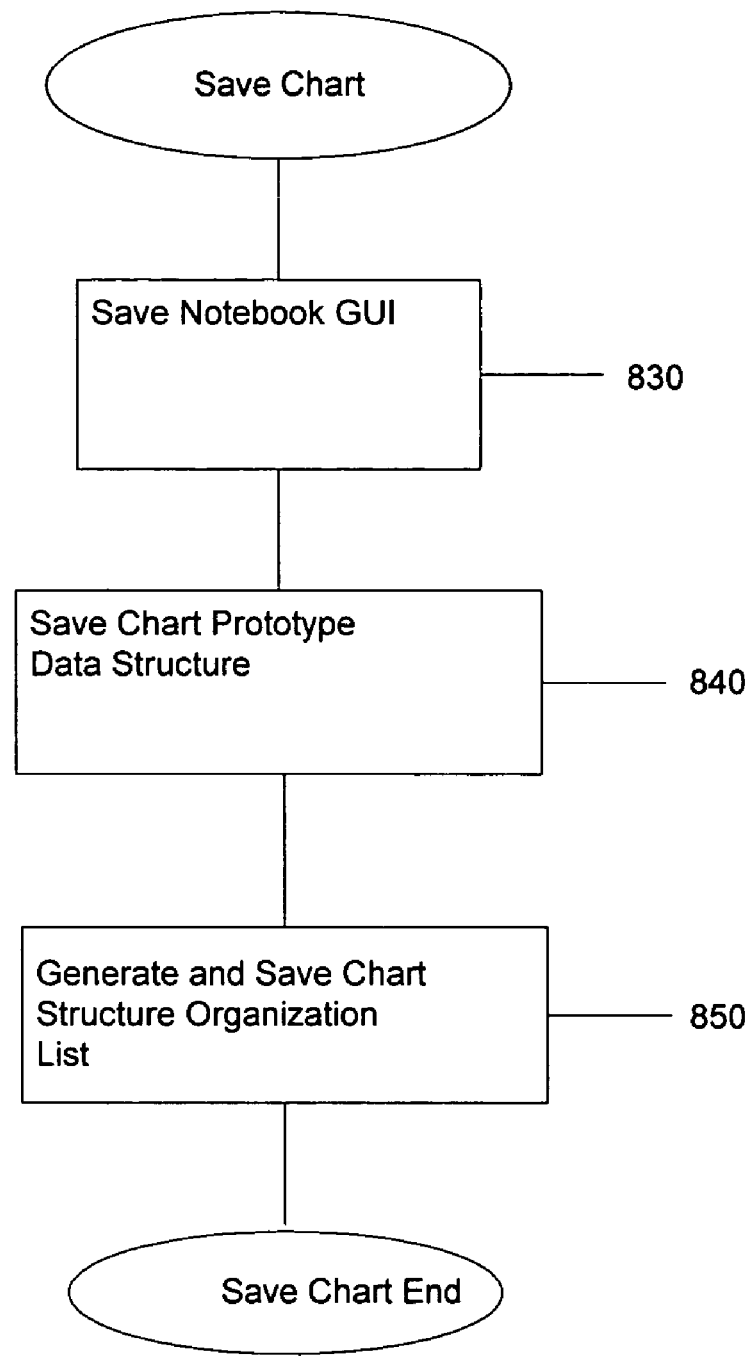
FIG. 14 shows an exemplary flow diagram for recording a chart in the Chart Maintenance Process according to an embodiment of the present invention.

In order to save a chart, the exemplary procedure shown in FIG. 14 can be used. In particular, the data for the notebook GUI widget can be recorded in an electronic storage arrangement (step 830). The chart prototype data structure can then be stored in step 840. In step 850, a chart structure organization list may be generated and recorded. An entry can preferably be created in the list for the corresponding charting entity nodes. The following table illustrates an exemplary cross-reference for the lists and the corresponding nodes according to the present invention:

| List | Node |
| --- | --- |
| Chart Prototype Encyclopedia | Chart Prototype |
| Forms Inventory | Forms |
| Sections Inventory | Sections |
| Charting Item Prototype Dictionary | Charting Item Prototype |

Patient Charting Process

An exemplary embodiment of a patient charting process according to the present invention shall be described in further details below. In particular, the patient charting process can be defined as the process for capturing and updating the patient information for a charting practice. The patient charting process can use a patient chart to process the patient information. The patient chart can be an instance of the chart prototype which allows the user to gather and process certain data for a particular patient. At any one time, there may be as many patient chart instances of the chart prototype as there are patients. However, it is preferable to have only one chart per patient. As discussed above, the chart prototype is preferably the specification (e.g., metadata) used to create the patient chart. These chart prototypes generally do not include the information regarding a patient, and are the blueprints or templates for the patient chart instances.

Figure 15:
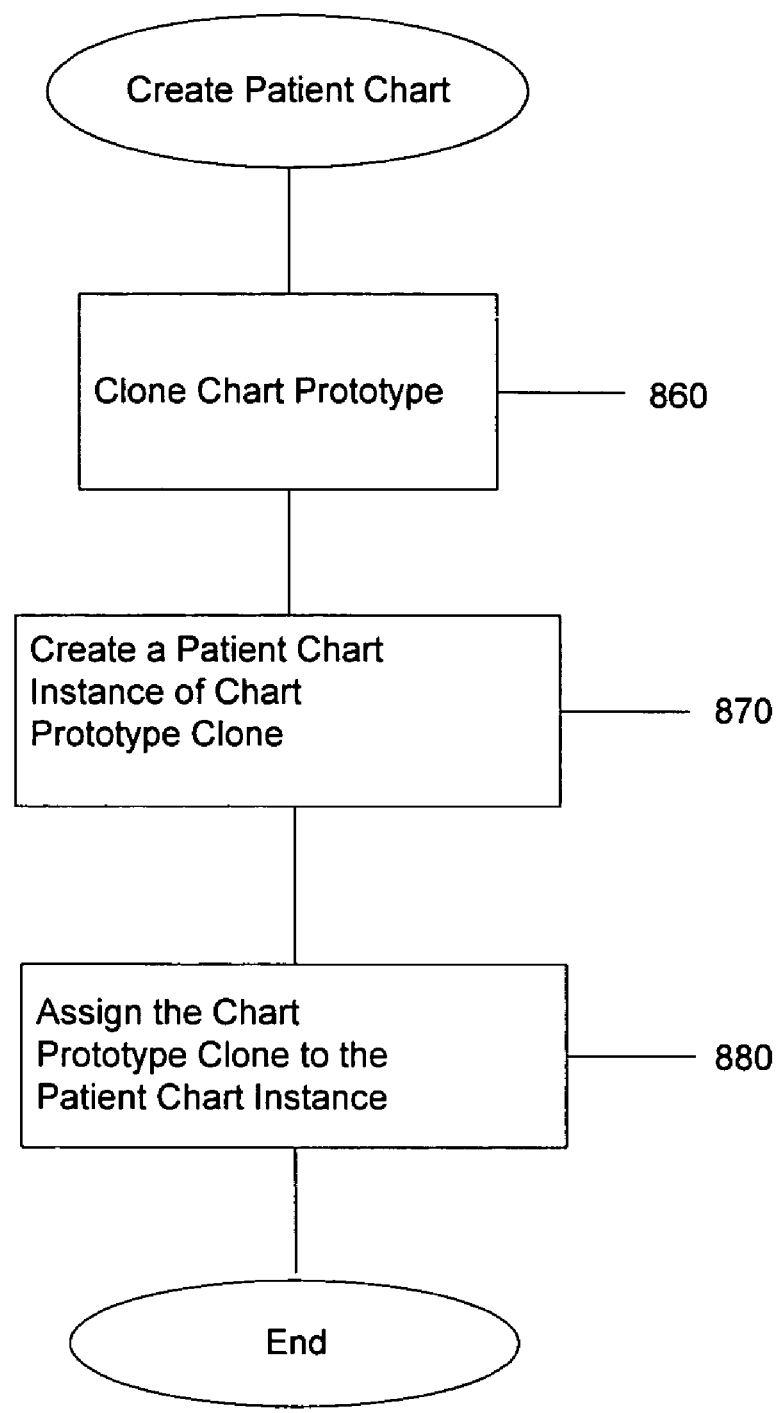
FIG. 15 shows an exemplary flow diagram for creating a patient chart instance from a patient chart prototype according to another embodiment of the present invention.

FIG. 15 shows an exemplary embodiment for a procedure which creates an instance of the patient chart according to the present invention. In particular, a clone of the chart prototype can be created in step 860. Then, in step 870, a patient chart instance of the chart prototype clone (generated in step 860) is created. Thereafter, in step 880, the chart prototype clone may be assigned to the patient chart instance.

Step 860 is preferably performed to ensure that the patient chart has its own structure, thus allowing modifications thereto without impacting the chart prototype. In addition, this cloning step allows a modification of the chart prototype, without impacting any of the patient chart instances that used such prototype. By providing the patient chart instance with its own chart prototype structure, the patient chart's dependence from the original chart prototype can be minimized or even removed. The patient chart would then include a clone of the chart prototype as its structure. In this manner, the patient chart instance may be modified by adding the Form, Section, and/or Charting Item Prototype thereto without effecting the underlying chart prototype structure and only effecting the clone of the underlying chart prototype that represents the patient chart instance. Indeed, such modification would only affect the individual instance of the patient chart and its corresponding structural model (i.e., the clone of the chart prototype), while the original chart prototype would remain unchanged. This procedure provides an easy way to customize and modify the charts for different patients, which may be advantageous whenever there are anomalies in the charting practice for such patients.

In the conventional systems and methods, all patient charts (i.e., instances) created from the original Chart prototype would require updates if the original chart prototype changed. This would be the case even for the changes made to the chart prototype which are not relevant to the previous instances of the chart prototype. The changes would nevertheless have to be propagated to those instances. Particularly, for the patient chart instances of the patients who have been discharged, it would not be preferable to propagate the changes to the charts of these patients after such discharge.

The independence from the patient chart instances according to the exemplary embodiment of the present invention also facilitates a creation of different versions of the chart prototype. This is the case because the changes to the original chart prototype are not passed to the current instances, but only to those instances that would be created by the new chart prototype version. By removing the inter-dependence of the chart prototypes and patient charts, a substantially more versatile system and process can be created. Indeed, according to the present invention, a clone of a chart prototype can be created by copying the chart prototype, along with each Form, Section and Chart Item Prototype.

Figure 16:
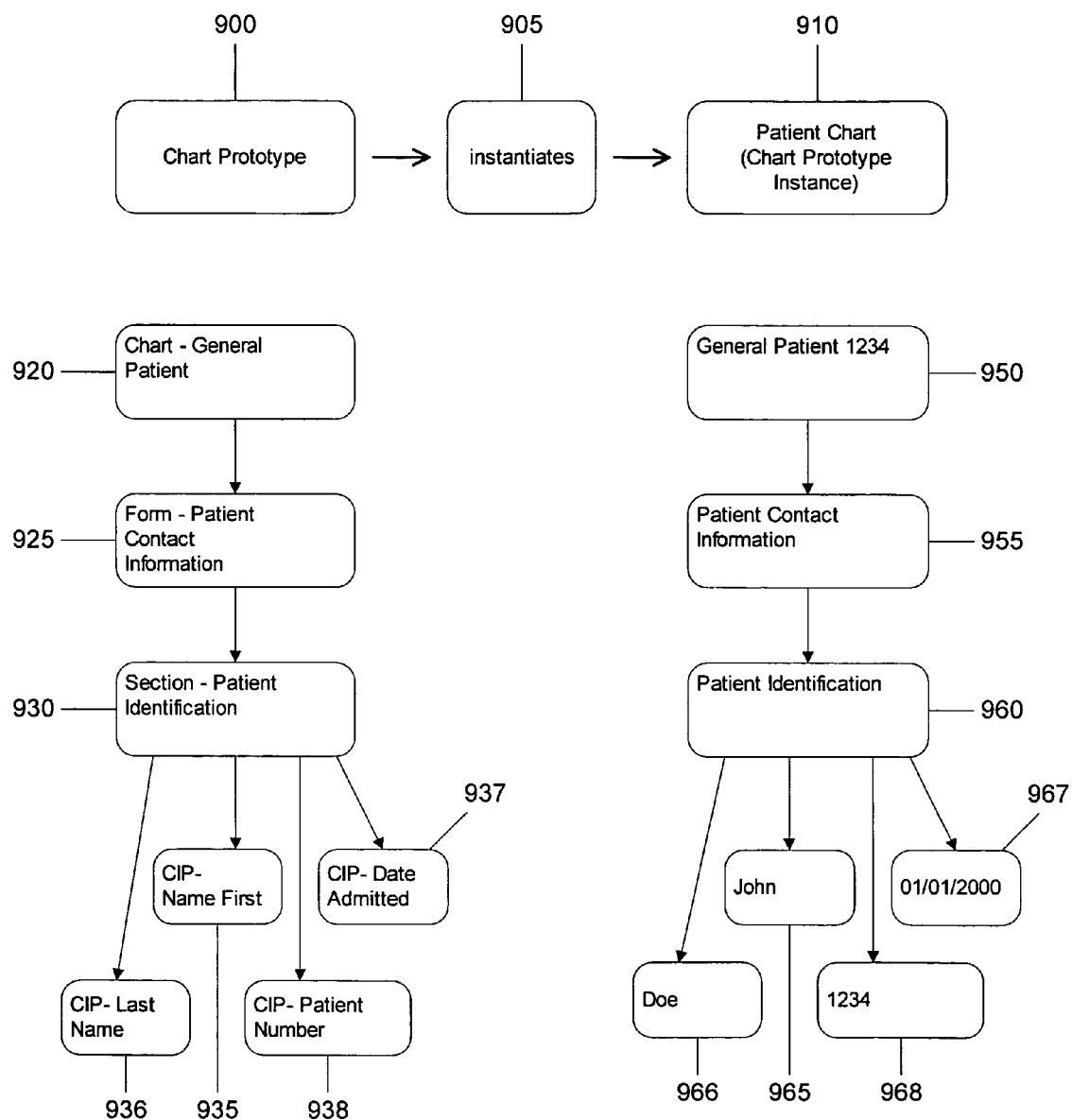
FIG. 16 shows an exemplary relationship between a patient chart prototype and a patient chart instance according to the embodiment of the present invention.

When the clone of the chart prototype is created, the patient chart can be instantiated from the clone. FIG. 16 illustrates the exemplary relationship between a chart prototype and an instance thereof. Items 920 through 938 are nodes within a chart prototype, and items 950 through 968 represent nodes within the instance of the prototype. While the nodes in the chart prototype act merely as templates, the nodes within the patient chart instance preferably contain actual data. As illustrated in FIG. 16, the Patient Chart instances are initially created with the default values for the charting items, as specified by the Charting Item Prototypes. For example, as a default, each patient chart instance is preferably given a "Patient ID", "Creation date" and "Creation user ID." When first instantiated, there is no actual patient information (i.e., only blank default values) in such patient chart instances. However, once instantiated in step 905, the patient chart may be used to record real patient information for the associated patient.

When the instantiation procedure 905 of the patient chart is performed, the clone 900 of the chart prototype is assigned to the patient chart in order to complete the creation of the patient chart. This chart prototype assignment will preferably allow the patient chart to have access to its data structure, and would enable the modification of the patient chart when necessary, without any impact on other patient charts or chart prototypes.

Changing a Patient Chart Instance

As provided in detail above, the patient chart may be modified by adding or deleting chart prototype data structure node entities (e.g., Forms, Sections, Charting Item Prototypes). For example, a patient being treated for an orthopedic disorder may initially have an instance of the patient chart which was created with an "orthopedic" chart prototype. This patient may later be discovered to have a neurological disorder, e.g., a side effect from his or her orthopedic disorder. The patient may then be scheduled to receive "neurological" care from a neurological specialist. At this point, the patient has changed from an "orthopedic" patient to an "orthopedic/neurological" patient. Neurological specialists have their own respective charting forms and practices required for their patients. The patient cannot have two different charts because the disorders are related, and each specialist should preferably have access to a complete history of the patient's health in order to effectuate the necessary treatment. In this exemplary case, the "orthopedic" patient chart instance would have to be changed to meet the new patient care needs for the neurological treatment, which would require, e.g., two additional Forms. To add these two neurological Forms, a change to the orthopedic patient chart instance would need to be implemented for that particular patient, without having an effect on the charts or charts structures of any other patients.

Figure 17:
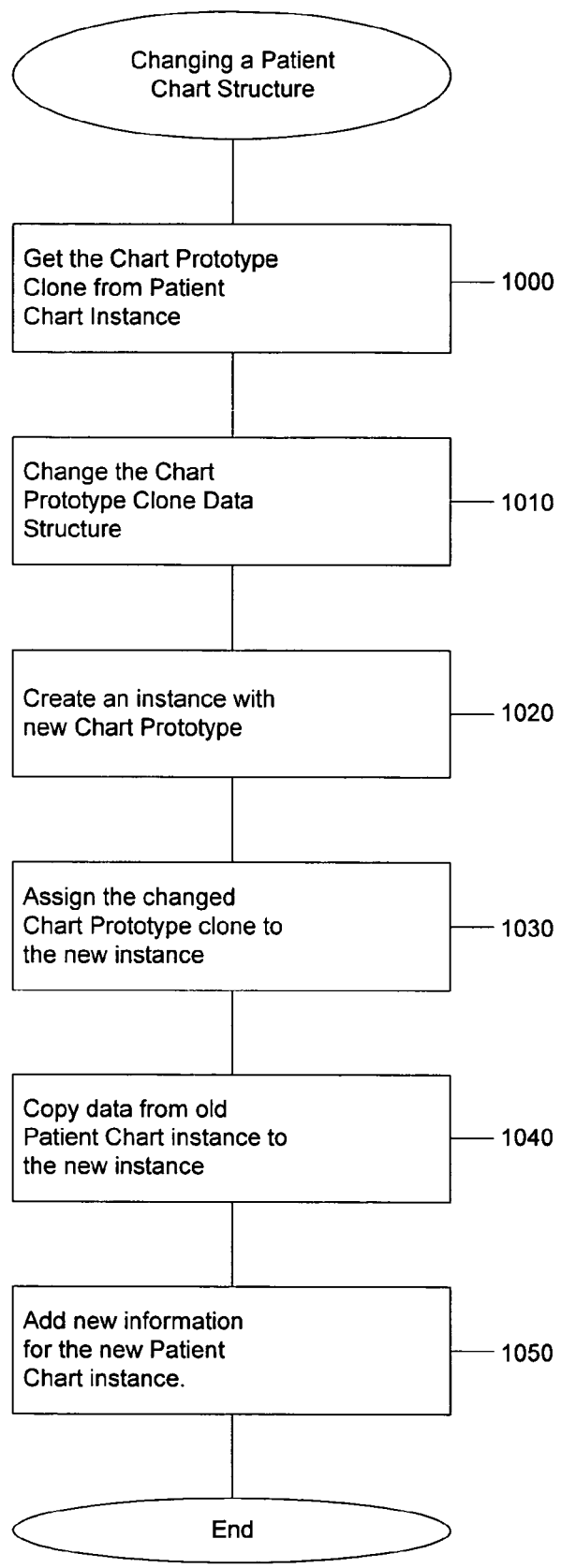
FIG. 17 shows an exemplary flow diagram for modifying a patient chart instance according to yet another embodiment of the present invention.

As shown in FIG. 17, an exemplary procedure to change a patient chart instance provides a six-step process. In step 1000, the chart prototype clone is obtained which was assigned to the patient chart instance after the instantiation thereof. Next, in step 1010, the modifications to the chart prototype clone are performed. In step 1020, a new patient chart instance is generated from the modified chart prototype clone. This modified chart prototype clone is then assigned to the new patient chart instance in step 1030. Thereafter, in step 1040, the information from the old patient chart instance is copied to the new patient chart instance. The new information for the patient chart instance can then be added in step 1050.

Persistence for Charts

In the exemplary embodiment of the present invention, the data persistence for the charts is preferably provided as follows. First, a Chart Structure Organization List (which is performed during the chart maintenance process) to represent the Chart Prototype Data Structure is created; and second, an Instance List (which is performed during the patient charting process) to represent the values of Chart Prototype instance is generated. These lists are generated by, e.g., "collapsing" (the inorder traversal of a composite pattern) the composite patterns or tree data structures (e.g., Chart Prototype Data Structure or Chart Prototype Instance) of the system and process into list form. This list may then be recorded in any manner, e.g., in a database, a spread sheet, a CSV file, etc. Thus, the system and process of the present invention can provide a complete independence from the selected means of storage, and preferably enables a high degree of flexibility to the user for selecting the type of the data storage method.

Figure 19:
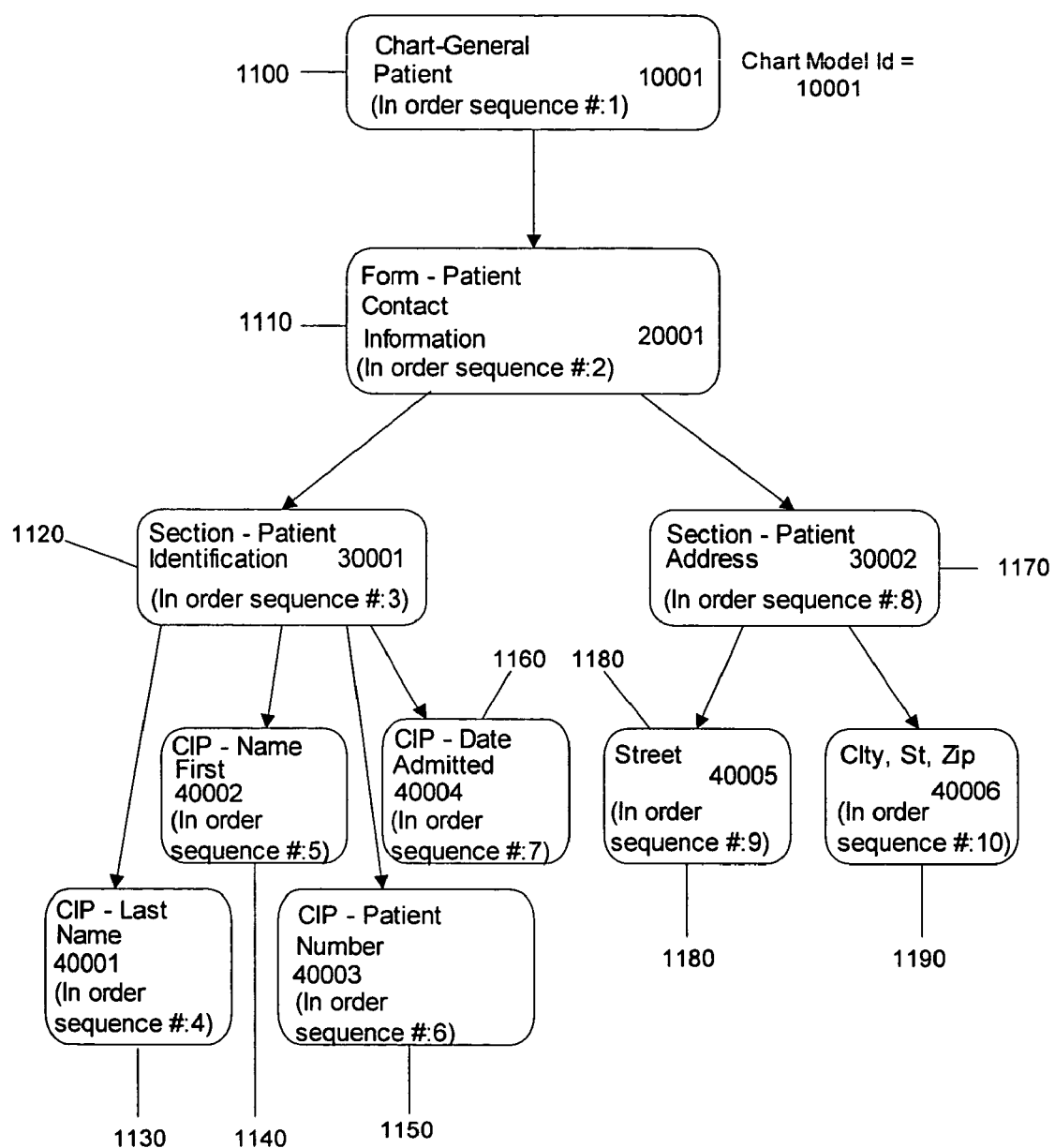
FIG. 19 shows an example of a chart prototype data structure with corresponding in order sequence numbers and component model identifications according to still another embodiment of the present invention.

When performing the persistence functions the Chart Structure Organization List can be used to create and/or validate the Instance List, and then the above-referenced lists are joined and cross-referenced against an exemplary Model Attribute Table to perform the conversions of data (e.g., to and from a data storage arrangement). This Model Attribute Table 1060, as shown in FIG. 18, can be populated each time a new node in the chart prototype data structure is created. The Model Attribute Table 1060 may interact with the charting item prototype dictionary for retrieving metadata definitions, as well as converting and defining the values for the charting items. The metadata definitions for the Sections, Forms and Chart Item Prototypes can also be added to the Model Attribute Table 1060. FIG. 19 shows an exemplary Chart Prototype Data Structure which includes a corresponding In-order sequence number and a component model ID.

FIG. 20 shows an exemplary embodiment of the corresponding cart structure organization list 1200 for the chart Prototype Data Structure of FIG. 19. The chart structure organization list 1200 can be created to be used for the process for persistence according to the present invention. This chart structure organization list 1200 is preferably a list comprised of three attributes per entry: the chart model ID, the In-order sequence number and the component model ID. The chart structure organization list 1200 can be generated by associating the chart model ID with the values for the component model ID and the In-order sequence number for all of the nodes visited during an inorder traversal of the chart prototype tree structure/composite data structure. All components in the chart prototype data structure may include a respective component model ID. The chart model ID is the component model ID for the first component visited during the inorder traversal, and is preferably the chart prototype.

Figure 21:
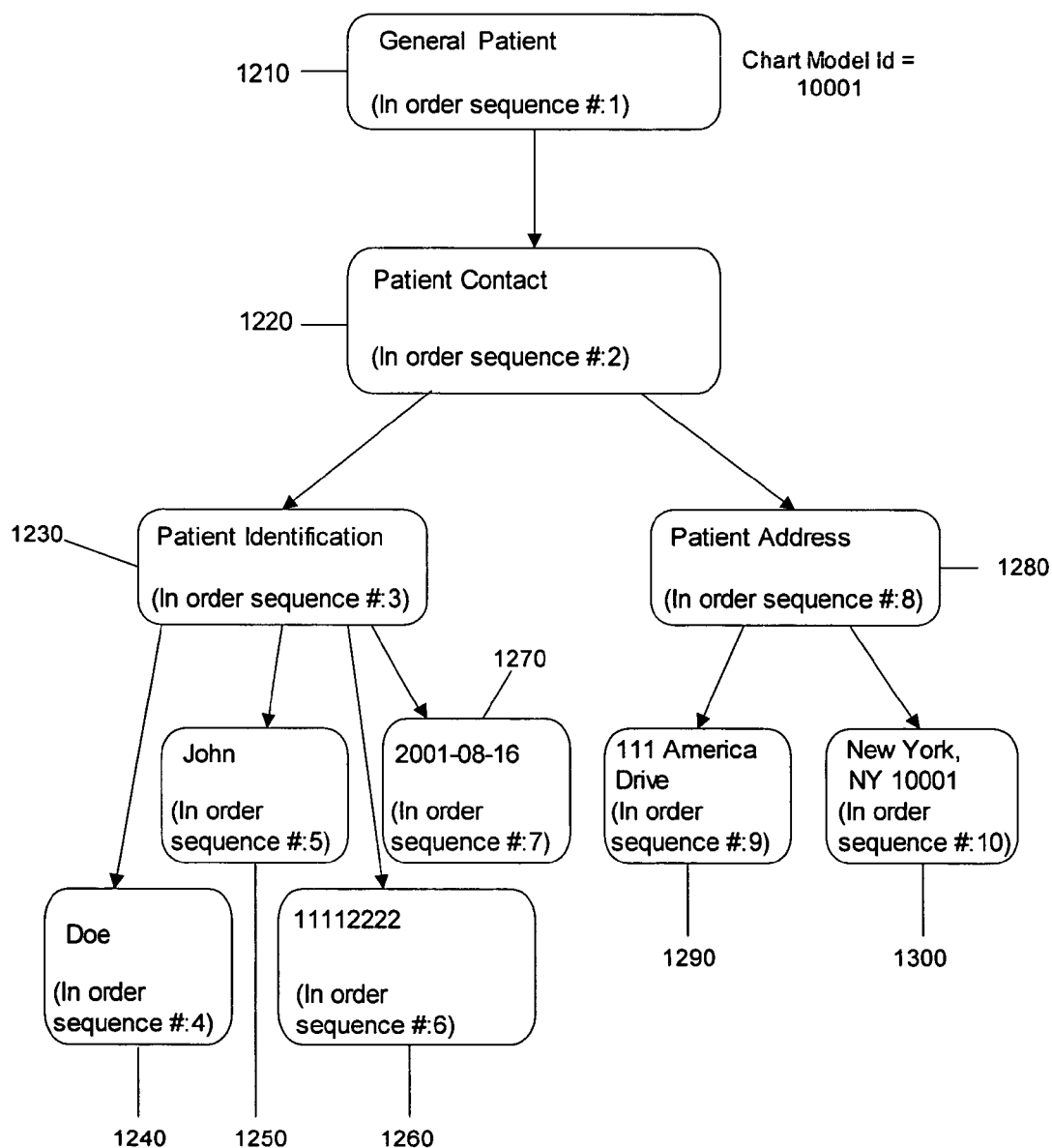
FIG. 21 shows an exemplary patient chart instance according to the present invention with corresponding inorder sequence numbers, instance numbers, chart model identification, and values.

FIG. 21 shows the exemplary Chart Prototype Data Structure illustrating the chart model ID, an instance number, values and corresponding In-order sequence numbers. According to the present invention, when the chart structure organization list 1200 is generated, an instance list 1400 of the chart prototype data structure can be created, an example of which is shown in FIG. 22. This instance list 1400 corresponds to the patient chart instance of FIG. 21 and may preferably be a list comprised of four attributes per entry: the chart model ID, the In-order sequence number, and the instance number and values. The list can be generated by associating the chart model ID with the values for the Inorder sequence number, the instance number and the values for all of the nodes visited during the Inorder traversal of the chart prototype data structure of the patient chart. The instance number is preferably a unique value assigned to the patient chart to distinguish it from all other instantiations of the same chart prototype.

Although the present invention has been described with certain embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. A process for creating and managing an application framework for a patient medical chart, comprising the steps of:

Generating at least one GUI (graphical user interface) structure simulating the appearance of a medical chart including at least one separate form for medical charting items and at least one separate form for non-medical charting items, and including a notebook GUI structure emulating a physical folder for maintaining electronic forms;

Simultaneously with said generating at least one GUI structure, generating at least one corresponding composite pattern data structure, Associating at least one node of the at least one composite data structure with an element of the at least one GUI structure based on charting item data contained in the at least one node, and visually indicating the association and charting item data type on the GUI;

Generating a copy of the at least one composite pattern data structure and producing at least one instance of the at least one copy of the at least one composite data structure, and representing the instance of the copy on the GUI indicating which specific instance it is, wherein the at least one copy of the at least one composite pattern data structure and the corresponding instance thereof are modified using the GUI without affecting the original version of the at least one composite pattern data structure as it existed prior to the modification while still visually changing the indication of the association and data type of the node on the GUI based on the modification; and Generating at least one list data structure corresponding to the at least one composite pattern data structure using an ordered sequence procedure, and recording the list data structure in a database.

* * * * *